(12) United States Patent
Kerl et al.

(10) Patent No.: US 10,092,502 B2
(45) Date of Patent: *Oct. 9, 2018

(54) OXIDATIVE HAIR LIGHTENERS WITH SPECIAL AMINATED SILICONE POLYMERS

(71) Applicant: Henkel AG & Co. KGaA, Duesseldorf (DE)

(72) Inventors: Sylvia Kerl, Hamburg (DE); Susanne Bietz, Elmshorn (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/454,084

(22) Filed: Mar. 9, 2017

(65) Prior Publication Data
US 2017/0172900 A1    Jun. 22, 2017

Related U.S. Application Data

(63) Continuation of application No. PCT/EP2015/068877, filed on Aug. 18, 2015.

(30) Foreign Application Priority Data

Sep. 9, 2014   (DE) ........................ 10 2014 217 999

(51) Int. Cl.
| | |
|---|---|
| *A61Q 5/10* | (2006.01) |
| *A61K 8/898* | (2006.01) |
| *A61Q 5/06* | (2006.01) |
| *A61K 8/34* | (2006.01) |
| *A61K 8/41* | (2006.01) |
| *A61K 31/13* | (2006.01) |

(52) U.S. Cl.
CPC ............. *A61K 8/898* (2013.01); *A61K 8/347* (2013.01); *A61K 8/41* (2013.01); *A61K 8/415* (2013.01); *A61K 31/13* (2013.01); *A61Q 5/065* (2013.01); *A61Q 5/10* (2013.01); *A61K 2800/4324* (2013.01); *A61K 2800/88* (2013.01); *A61K 2800/882* (2013.01)

(58) Field of Classification Search
CPC .......... A61Q 5/10; A61Q 5/065; A61K 8/898; A61K 8/415; A61K 8/41; A61K 8/347; A61K 2800/4324; A61K 2800/88; A61K 2800/882
See application file for complete search history.

(56) References Cited

U.S. PATENT DOCUMENTS

| | | | |
|---|---|---|---|
| 6,596,035 B2 * | 7/2003 | Gutkowski | ............... A61K 8/22 8/110 |
| 2003/0152534 A1 * | 8/2003 | Legrand | ................... A61K 8/35 424/61 |
| 2003/0229947 A1 | 12/2003 | Clarke et al. | |
| 2007/0261178 A1 | 11/2007 | Rondeau et al. | |
| 2014/0190999 A1 * | 7/2014 | Weser | ...................... A61K 8/42 8/405 |

FOREIGN PATENT DOCUMENTS

| | | |
|---|---|---|
| EP | 1464321 A1 | 10/2006 |
| EP | 2895242 A1 | 6/2007 |
| WO | 02/47632 A2 | 6/2002 |
| WO | 03/009822 A2 | 2/2003 |
| WO | 2012/079915 A2 | 6/2012 |

OTHER PUBLICATIONS

STIC Search Report dated Apr. 24, 2017.*
PCT International Search Report (PCT/EP2015/068877) dated Oct. 13, 2015.
Liu X. M. et. al.; "Comparative Studies of Poly(DimethylSiloxanes) Using Automated GPC-MALDI-TOF MS and On-Line GPC-ESI-TOF MS"; Am. Soc. Mass. Spectrom_2003_14_195—202.

\* cited by examiner

*Primary Examiner* — Eisa B Elhilo
(74) *Attorney, Agent, or Firm* — P. Scott Smith

(57) ABSTRACT

The present invention relates to a cosmetic agent for dyeing, in particular for lightening keratin fibers, in particular human hair, including at least one specific aminated silicone polymer and at least one oxidation dye intermediate and/or one direct dye, wherein the use of the at least one aminated silicone polymer leads to improved care of the keratin fibers with improved hair lightening performance. The invention further relates to a corresponding packaging unit (kit of parts) and to a method for dyeing, in particular lightening, of keratin fibers. Lastly, the invention relates to the use of the cosmetic agent according to the invention and the use of a packaging unit for producing an oxidative hair lightener for care of keratin fibers with improved lightening performance.

16 Claims, No Drawings

OXIDATIVE HAIR LIGHTENERS WITH SPECIAL AMINATED SILICONE POLYMERS

FIELD OF THE INVENTION

The present invention relates to cosmetic agents for dyeing, in particular for lightening keratin fibers, including specific aminated silicone polymers.

The present invention also relates to a packaging unit (kit of parts) including a cosmetic agent according to the invention and an oxidizing agent preparation.

The present invention additionally relates to a method for dyeing, in particular for lightening keratin fibers with use of a cosmetic agent according to the invention and also an oxidizing agent preparation.

The present invention also relates to the use of a cosmetic agent according to the invention for increasing the care of keratin fibers with improved lightening performance.

Lastly, the present invention relates to the use of a packaging unit according to the invention for producing a cosmetic agent for changing the color of, in particular for lightening keratin fibers with increased care of the keratin fibers with improved lightening performance.

BACKGROUND OF THE INVENTION

Changing the shape and color of hair is an important field of modern cosmetics. The appearance of the hair can thus be adapted both to current trends and to the individual desire of the individual consumer. Consumers turn to color-changing agents for the fashionable coloring of hairstyles or to cover grey or even white hair with fashionable or natural color shades. In addition to a high coloring performance, these agents should have additional properties, such as increasing the volume of the hair.

Various coloring systems are known in the prior art in order to provide color-changing cosmetic agents, in particular for the skin or for keratin-containing fibers, such as human hair.

Oxidation dyes are used for permanent intense colorings having appropriate fastness properties. Such dyes usually include oxidation dye precursors, or what are known as developer components and coupler components. The developer components form the actual dyes under the influence of oxidizing agents or atmospheric oxygen with one another or with coupling to one or more coupler components. The oxidation dyes are indeed characterized by excellent, long-lasting color results. However, for naturally acting dyes, a mixture of a larger number of oxidation dye precursors has to be used; in many cases direct dyes are also used for providing color variations.

Dyes or toners which include what are known as direct dyes as coloring component are usually used for temporary colorings. Direct dyes are dye molecules which are drawn directly onto the substrate and do not require an oxidative process in order to form the color. These dyes include, for example, henna, which is already known from ancient times for coloring the body and hair. These dyes are generally much more sensitive to shampooing than oxidative dyes, and therefore a change in color or a visible loss of homogenous color, which is undesirable for many reasons, occurs much earlier.

Lastly, a further coloring method has drawn much attention. In this method, precursors of the natural hair colorant melanin are applied to the substrate, for example hair; these then form dyes similar to natural dyes within the scope of oxidative processes in the hair. In such a method, 5,6-dihydroxyindolin for example is used as dye precursor. In particular, with multiple application of agents comprising 5,6-dihydroxyindolin, it is possible to reinstate the natural hair color in individuals that have grey hair. The coloration can be provided here with atmospheric oxygen as sole oxidizing agent, such that it is possible to dispense with further oxidizing agents. In individuals having originally medium-blond to brown hair, 5,6-dihydroxyindolin can be used as the sole dye precursor. For use in individuals having originally red and in particular dark to black hair color, satisfactory results can be attained by contrast often only by co-use of further dye components, in particular specific oxidation dye precursors.

The dyes known in the prior art, however, do not always lead to the desired high coloring performance, in particular lightening performance, or have additional desired properties, such as improved care of the hair during the hair-coloring process.

BRIEF SUMMARY OF THE INVENTION

The object of the present invention was therefore to provide a cosmetic agent for coloring, in particular for lightening keratin fibers which avoids or at least mitigates the disadvantages of the prior art and which results in improved care of the hair with improved lightening performance.

Furthermore, other desirable features and characteristics of the present invention will become apparent from the subsequent detailed description of the invention and the appended claims, taken in conjunction with this background of the invention.

A first subject of the invention is therefore a cosmetic agent for changing the color of, in particular for lightening keratin fibers, comprising, in a cosmetically acceptable carrier a) at least one compound, selected from the group of oxidation dye precursors, direct dyes, and mixtures thereof, b) at least one aminated silicone polymer, including at least one structural unit of formula (I) and at least one structural unit of formula (II)

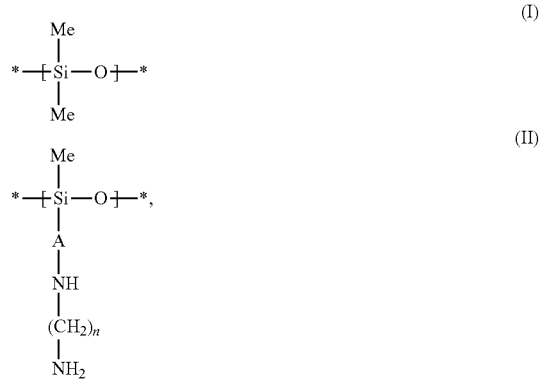

in which
A stands for a linear or branched $C_4$-$C_8$ alkyl group, and
n stands for integers from 1 to 4,
wherein the cosmetic agent does not include any acid selected from the group of carboxylic acids having 8 to 30 carbon atoms, ether carboxylic acids having 8 to 30 carbon atoms, ether phosphoric acids having 8 to 30 carbon atoms, phosphoric acids having 8 to 30 carbon atoms, and mixtures thereof.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now surprisingly been found that the addition of at least one specific aminated silicone polymer in cosmetic agents for coloring, in particular for lightening keratin fibers, in particular human hair, leads to an improved care, in particular to an improved combability, with improved lightening performance.

In accordance with the above formulas and all subsequent formulas, a chemical bond characterized by the symbol "*" stands for a free valence of the corresponding structure fragment. Here, a "free valence" is understood to mean the number of atomic bonds emanating from the corresponding structure fragment in the position characterized by the symbol "*". Within the scope of the present invention, an atomic bond preferably emanates from each of the positions of the structure fragments characterized by the symbol "*" to further structure fragments.

The term "keratin fibers" is understood in accordance with the invention to mean fur, wool and feathers and also human hair. It is particularly preferred within the scope of the present invention if the cosmetic agents are used for the dyeing of human hair.

Within the scope of the present invention, the term "aminated silicone polymers" is also understood to mean silicone polymers which have at least one amino group per silicone polymer.

In addition, the term "combability" within the scope of the present invention is understood to mean both the combability of the wet fibers and also the combability of the dry fibers.

In accordance with the invention, "carboxylic acids having 8 to 30 carbon atoms" include carboxylic acids of formula R—COOH, in which R stands for a linear or branched, saturated or unsaturated alkyl group having 8 to 30 carbon atoms. Examples of carboxylic acids of this type are, for example, capric acid, lauric acid, coconut acid, stearic acid, isostearic acid, linolenic acid, oleic acid, myristic acid, olive oil acid, and the like. The group of ether carboxylic acids having 8 to 30 carbon atoms includes, in accordance with the invention, compounds of formula RO[CH2O]u[(CH2)xCH(R')(CH2)y(CH2)zO]v[CH2CH2O]wCH2COOH, in which R stands for a linear or branched, saturated or unsaturated alkyl group having 8 to 30 carbon atoms, R' stands for a hydroxyl group, or an alkyl group, u, v and w, each independently of one another, stand for integers from 0 to 60, and x, y and z, each independently of one another, each stand for integers from 0 to 13, wherein the sum x+y+z≥0. Examples of such ether carboxylic acids are, for example, the compounds known under the INCI names Laureth-4 Carboxylic Acid, PPG-6-Laureth-6 Carboxylic Acid, Steareth-7 Carboxylic Acid, Oleth-10 Carboxylic Acid, Trideceth-6 Carboxylic Acid, Undeceth-5 Carboxylic Acid and the like. Ether phosphoric acids having 8 to 30 carbon atoms within the scope of the present invention fall under the formula {RO[CH2O]u[(CH2)xCH(R')(CH2)y(CH2)zO]v[CH2CH2O]w}a-PO—(OH)b, in which R stands for a linear or branched, saturated or unsaturated alkyl group having 8 to 30 carbon atoms, R' stands for a hydroxyl group or an alkyl group, u, v and w, each independently of one another, stand for integers from 0 to 60, x, y, and z, each independently of one another, stand for integers from 0 to 13, b stands for the integer 0 when a stands for the integer 2, and b stands for the integer 2 when a stands for the integer 0, wherein the sum x+y+x≥0. Examples of such ether phosphoric acids are, for example, PPG-5-Ceteth-10 phosphate, Oleth-3 phosphate and the like. Lastly, in accordance with the invention, the group of phosphoric acids having 8 to 30 carbon atoms includes compounds of formula R—O—P(O)(OH)2, in which R stands for a linear or branched, saturated or unsaturated alkyl group having 8 to 30 carbon atoms. Examples of such phosphoric acids are Capryl Phosphate, Lauryl Phosphate, Oleyl Phosphate, Isostearyl Phosphate, Stearyl Phosphate and Cetyl Phosphate, for example.

In addition, the term "fatty alcohols" within the scope of the present invention is understood to mean aliphatic, long-chain, monovalent, primary alcohols comprising unbranched hydrocarbon groups having 6 to 30 carbon atoms. The hydrocarbon groups can be saturated, but can also be mono- or polyunsaturated.

Lastly, the term "fatty acids" within the scope of the present invention is understood to mean aliphatic monocarboxylic acids with unbranched carbon chain which comprise hydrocarbon groups having 6 to 30 carbon atoms. The hydrocarbon groups can be either saturated or mono- or polyunsaturated.

The specification of the total amount in relation to the components of the cosmetic agent relates in the present case—unless specified otherwise—to the total amount of active substance of the respective components. Furthermore, the specification of the total amount in relation to the components of the cosmetic agent—unless specified otherwise—relates to the total weight of the cosmetic agent according to the invention free from oxidizing agent.

The cosmetic agents according to the invention include a cosmetic carrier. In accordance with the invention, the cosmetic carrier is preferably aqueous, alcoholic, or aqueous-alcoholic. Within the scope of the present invention, creams, emulsions, gels or surfactant-containing foaming solutions, such as shampoos, foam aerosols, or other preparations suitable for application to the hair, can be used.

An aqueous carrier in the sense of the invention includes at least 30% by weight, in particular at least 50% by weight of water, in relation to the total weight of the cosmetic agent.

Aqueous-alcoholic carriers within the sense of the present invention are understood to mean water-containing compositions including a C1-C4 alcohol in a total amount of from 3 to 90% by weight, in relation to the total weight of the cosmetic agent, in particular ethanol or isopropanol.

The agents according to the invention can additionally include further organic solvents, such as methoxybutanol, ethyldiglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred here, wherein the solvent is included in a total amount of from 0.1 to 30% by weight, preferably from 1 to 20% by weight, in particular from 2 to 10% by weight, in relation to the total weight of the cosmetic agent.

The cosmetic agent according to the invention includes, as first essential constituent a), a compound selected from the group of oxidation dye precursors (ODPs), direct dyes (DDs), and mixtures thereof.

In a preferred embodiment cosmetic agents according to the invention include at least one oxidation dye precursor.

Oxidation dye precursors can be divided into two categories on the basis of their reaction behavior: what are known as developer components and coupler components. Developer components can form the actual dye in themselves. They can therefore be included as the sole compounds in the cosmetic agent according to the invention. In a preferred embodiment the cosmetic agents according to the invention therefore include at least one oxidation dye precursor of the developer type. However, it can also be provided within the scope of the present invention that the cosmetic agents according to the invention include at least one oxidation dye precursor of the coupler type. Particularly good results in respect of the coloring of keratin fibers are obtained if the cosmetic agents according to the invention include at least one oxidation dye precursor of the developer type and at least one oxidation dye precursor of the coupler type.

The developer and coupler components are usually used in free form. In the case of substances with amino groups, however, it can be preferred to use the salt form thereof, in particular in the form of the hydrochlorides and hydrobromides or the sulfates.

In accordance with the invention, cosmetic agents that are preferred are those which include the developer and/or coupler components in each case in a total amount of from 0.001 to 10% by weight, preferably from 0.01 to 8% by weight, preferably from 0.1 to 5% by weight, in particular from 0.5 to 3% by weight, in relation to the total weight of the cosmetic agent.

In a further preferred embodiment, the cosmetic agent according to the invention is therefore characterized in that it includes an oxidation dye precursor of the developer and/or coupler type in a total amount of from 0.001 to 10% by weight, preferably from 0.01 to 8% by weight, preferably from 0.1 to 5% by weight, in particular from 0.5 to 3% by weight, in relation to the total weight of the cosmetic agent.

Suitable oxidation dye precursors of the developer type are, for example, p-phenylenediamine and derivatives thereof. Preferred p-phenylenediamines are selected from one or more compounds of the group formed from p-phenylenediamine, p-toluenediamine, 2-chloro-p-phenylenediamine, 2,3-dimethyl-p-phenylenediamine, 2,6-dimethyl-p-phenylenediamine, N,N-bis-(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine and N-(4-amino-3-methyl-phenyl)-N-[3-(1H-imidazol-1-yl)propyl] amine as well as the physiologically acceptable salts thereof.

In accordance with the invention, it can also be preferred to use, as developer components, compounds that include at least two aromatic nuclei substituted with amino and/or hydroxyl groups. Preferred binuclear developer components are selected from N,N'-bis-(2-hydroxyethyl)-N,N'-bis-(4'-aminophenyl)-1,3-diaminopropan-2-ol, N,N'-bis-(4-aminophenyl)-1,4-diazacycloheptane, bis-(2-hydroxy-5-aminophenyl) methane as well as the physiologically acceptable salts thereof.

It can also be preferred in accordance with the invention to use, as developer components, a p-aminophenol derivative or a physiologically acceptable salt thereof. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and physiologically acceptable salts thereof.

The developer component can also be selected from o-aminophenol and derivatives thereof, preferably from 2-amino-4-methylphenol, 2-amino-5-methylphenol, 2-amino-4-chlorophenol, and/or physiologically acceptable salts thereof.

The developer component can also be selected from heterocyclic developer components, such as pyrimidine derivatives, pyrazole derivatives, pyrazolopyrimidine derivatives and the physiologically acceptable salts thereof. Preferred pyrimidine derivatives are 2,4,5,6-tetraaminopyrimidine, 4-hydroxy-2,5,6-triaminopyrimidine and the physiologically acceptable salts thereof. A preferred pyrazole derivative is 4,5-diamino-1-(2-hydroxyethyl) pyrazole and the physiologically acceptable salts thereof. In particular, pyrazolo[1,5-a]pyrimidines are preferred as pyrazolopyrimidines.

Preferred oxidation dye precursors of the developer type are selected from the group formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)¬phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of these compounds.

Particularly preferred developer components are p-toluenediamine, 2-(2-hydroxyethyl)-p-phenylenediamine, 2-methoxymethyl-p-phenylenediamine, N-(4-amino-3-methylphenyl)-N[3-(1H-imidazol-1-yl)propyl]amine, and/or 4,5-diamino-1-(2-hydroxyethyl)-pyrazole and the physiologically acceptable salts thereof.

In accordance with a further preferred embodiment of the present invention, besides at least one developer component, the cosmetic agent according to the invention includes, as oxidation dye precursor, also additionally at least one coupler component. Generally, m-phenylenediamine derivatives, naphthols, resorcinol and resorcinol derivatives, pyrazolones and m-aminophenol derivatives are used as coupler components.

Coupler components that are preferred in accordance with the invention are selected from
a) m-aminophenol and/or derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)-amino-2-methylphenol and 2,4-dichloro-3-aminophenol,
b) o-aminophenol and derivatives thereof, such as 2-amino-5-ethylphenol,
c) m-diaminobenzene and/or derivatives thereof, such as 2,4-diaminophenoxyethanol, 1,3-bis-(2',4'-diaminophenoxy)propane, 1-methoxy-2-amino-4-(2'-hydroxyethylamino)benzene, 2,6-bis(2'-hydroxyethylamino)-1-methylbenzene, 2-({3-[(2-hydroxyethyl)amino]-4-methoxy-5- methylphenyl}amino)ethanol, and 2-({3-[(2-hydroxyethyl)amino]-2-methoxy-5-methylphenyl}-amino)ethanol,
d) o-diaminobenzene and derivatives thereof,
e) di- or trihydroxybenzene derivatives, in particular resorcinol, 2-chlororesorcinol, 4-chlororesorcinol, 2-methylresorcinol, and 1,2,4-trihydroxybenzene,
f) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine,
g) naphthalene derivatives, such as 1-naphthol and 2-methyl-1-naphthol,
h) morpholine derivatives, such as 6-hydroxybenzomorpholine,
i) quinoxaline derivatives,
j) pyrazole derivatives, such as 1-phenyl-3-methylpyrazol-5-one,
k) indol derivatives, such as 6-hydroxyindol,
l) pyrimidine derivatives, or
m) methylenedioxybenzene derivatives, such as 1-(2'-hydroxyethyl)-amino-3,4-methylenedioxybenzene as well as the physiologically acceptable salts thereof.

Coupler components that are preferred in accordance with the invention are selected from the group formed from 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)-amino-2-methyl phenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dhydroxynaphthalene, 2,7-dihydroxynaphthalene, 1,7-dihydroxynaphthalene, 1,8-dihydroxynaphthalene, 4-hydroxyindol, 6-hydroxyindol, 7-hydroxyindol, 4-hydroxyindolin, 6-hydroxyindolin, 7-hydroxyindolin, and/or the physiologically acceptable salts of the aforesaid compounds.

Coupler components that are particularly preferred in accordance with the invention are resorcinol, 2-methylresorcinol, 4-chlororesorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, and 1-naphthol as well as the physiologically acceptable salts thereof.

In a particularly preferred embodiment of the present invention, the cosmetic agents according to the invention are characterized in that they include, as oxidation dye precursor, at least one developer component selected from the group of p-phenylenediamine, p-toluenediamine, N,N-bis-(2-hydroxyethyl)amino-p-phenylenediamine, 1,3-bis-[(2-hydroxyethyl-4'-aminophenyl)amino]-propan-2-ol, 1,10-bis-(2',5'-diaminophenyl)-1,4,7,10-tetraoxadecane, 4-aminophenol, 4-amino-3-methylphenol, bis-(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)pyrazole, the physiologically acceptable salts thereof and mixtures thereof, and at least one coupler component selected from the group of resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorophenol, 2,4-diaminophenoxyethanol, 2-amino-4-(2'-hydroxyethyl)amino-anisolsulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-one, 2,6-bis-[(2'-hydroxyethyl)amino]toluene, 4-hydroxyindole, 6-hydroxyindole, 6-hydroxybenzomorpholine, the physiologically acceptable salts thereof, and mixtures thereof.

In order to obtain a balanced and subtle shading, it can also be provided within the scope of the present invention that the cosmetic agents according to the invention additionally include at least one direct dye. Direct dyes are dyes which are drawn directly onto the hair and which do not require an oxidative process in order to form the color. Direct dyes are usually nitrophenylenediamines, nitroaminophenols, azo dyes, anthraquinones or indophenols.

Direct dyes can be divided into anionic, cationic, and non-ionic direct dyes.

Preferred anionic direct dyes are the compounds known under the names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol. Preferred cationic direct dyes are cationic triphenylmethane dyes such as Basic Blue 7, Basic Blue 26, Basic Violet 2 and Basic Violet 14 and aromatic systems which are substituted with a quaternary nitrogen group, such as Basic Yellow 57, Basic Red 76, Basic Blue 99, Basic Brown 16 and Basic Brown 17 and HC Blue 16, and Basic Yellow 87, Basic Orange 31 and Basic Red 51. Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis (2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Furthermore, dyes occurring in nature can be used as direct dyes, such as those included for example in henna red, henna neutral, henna black, chamomile blossom, sandalwood, black tea, walnut, cascara bark, sage, logwood, madder root, catechu, and alkanet root.

The cosmetic agent according to the invention preferably includes the direct dyes in a total amount of from 0.001 to 10% by weight, preferably from 0.01 to 8% by weight, preferably from 0.1 to 5% by weight, in particular from 0.5 to 3% by weight, in relation to the total weight of the cosmetic agent.

As second essential constituent b), the cosmetic agents according to the invention include at least one specific aminated silicone polymer. The addition of this/these specific silicone polymer(s) leads to improved care, in particular improved wet combability, with improved lightening performance of the cosmetic agents according to the invention.

In accordance with a preferred embodiment of the present invention, in the structural unit of formula (II), n stands for the integer 2 or 3, in particular for the integer 2, and A stands for a branched C4 alkyl group, in particular an isobutyl group.

In accordance with the invention, the cosmetic agent particularly preferably includes at least one aminated silicone polymer of formula (III)

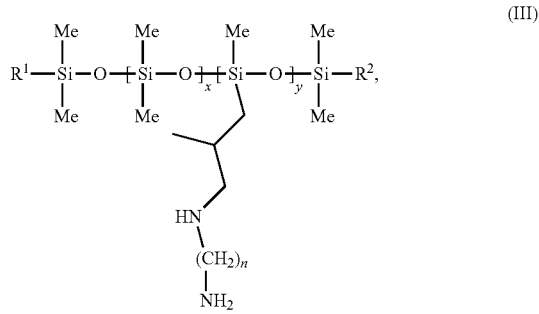

in which

R1 and R2, each independently of one another, stand for a methyl group or a hydroxyl group, x stands for integers from 0 to 1,999, preferably from 4 to 1,500, preferably from 10 to 1,000, more preferably from 20 to 500, in particular from 49 to 149, y stands for integers from 1 to 200, preferably from 1 to 70, preferably from 1 to 50, more preferably from 1 to 30, in particular from 1 to 10, and n stands for integers from 1 to 5, preferably from 1 to 4, preferably from 1 to 3, in particular 2 or 3. The use of these specific aminated silicone polymers results in increased care of the keratin fibers, in particular increased wet combability after the change in color, in particular lightening, and at the same time leads to improved lightening.

The at least one aminated silicone polymer b) preferably has a mean molecular weight Mw of from 350 to 350,000 Da, preferably from 500 to 300,000 Da, preferably from 700 to 250,000 Da, in particular from 1,000 to 200,000 Da. Specific aminated silicone polymers having the aforementioned mean molecular weight Mw result in a particularly high care of keratin fibers after the change in color, with improved lightening performance. The mean molecular weight Mw can be determined for example by gel permeation chromatography (GPC) (Liu X. M. et al.; "Comparative Studies of Poly(DimethylSiloxanes) Using Automated GPC-MALDI-TOF MS and On-Line GPC-ESI-TOF MS"; Am. Soc. Mass. Spectrom., 2003, 14, pages 195 to 202).

It has proven to be advantageous if the at least one aminated silicone polymer b) has an amine value above 0.25 meq/g, preferably above 0.3 meq/g, in particular above 0.4 meq/g.

Within the scope of the present invention, it is particularly preferred if the at least one aminated silicone polymer b) has an amine value of from 0.25 to 5 meq/g, preferably from 0.3 to 4.5 meq/g, preferably from 0.4 to 4.0 meq/g, more preferably from 0.5 to 3.0 meq/g, in particular from 0.5 to 1.5 meq/g. The amine value stands here for the milliequivalents of amine per gram of the aminofunctional silicone. It can be determined by titration and can also be specified in the unit mg KOH/g. The use of aminated silicone polymers having the aforementioned amine values results in a particularly high care of the keratin fibers treated using the cosmetic agents according to the invention. With use of silicone polymers having amine values within the aforementioned ranges, an excellent lightening performance of the cosmetic agents according to the invention is also achieved.

The at least one aminated silicone polymer b) is included in the cosmetic agents according to the invention in a total amount of from 0.0001 to 15% by weight, preferably from 0.0005 to 10% by weight, preferably from 0.005 to 5.0% by weight, more preferably from 0.01 to 3.0% by weight, in particular from 0.05 to 1.0% by weight, in relation to the total weight of the cosmetic agent. The use of the aforementioned total amount of the specific aminated silicone polymer leads to an increased care of the keratin fibers with excellent lightening performance.

It has been found that an addition of cyclic aminated silicone polymers is particularly advantageous within the scope of the present invention. Cosmetic agents that are preferred in accordance with the invention therefore additionally include a cyclic aminated silicone polymer in a total amount of from 0.003 to 1.5% by weight, preferably from 0.006 to 1.1% by weight, preferably from 0.009 to 0.8% by weight, more preferably from 0.01 to 0.5% by weight, in particular from 0.015 to 0.3% by weight, in relation to the total weight of the cosmetic agent, wherein the cyclic aminated silicone polymer has the formula (IV)

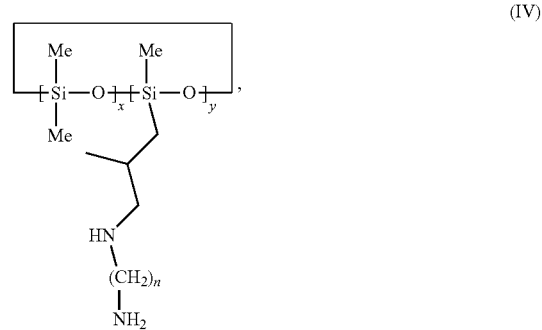

in which x stands for integers from 0 to 1,999, preferably from 4 to 1,500, preferably from 10 to 1,000, more preferably from 20 to 500, in particular from 49 to 149, and y stands for integers from 1 to 200, preferably from 1 to 70, preferably from 1 to 50, more preferably from 1 to 30, in particular from 1 to 10. The addition of aminated cyclic silicone polymers can further increase the care effect and also the lightening performance of the cosmetic agents according to the invention.

The addition of dimethylcyclosiloxanes has also proven to be advantageous. It is therefore preferred within the scope of the present invention if the cosmetic agents according to the invention additionally include dimethylcyclosiloxane in a total amount of less than 1% by weight, in relation to the total weight of the cosmetic agent, wherein the dimethylcyclosiloxane has the formula (V)

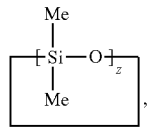

(V)

in which
z stands for integers from 2 to 8, preferably from 2 to 6, in particular for 3, 4, 5 or 6. The addition of dimethylcyclosiloxanes to the cosmetic agents according to the invention leads to a further improvement of the caring performance and the lightening performance of the cosmetic agents according to the invention.

The cosmetic agents according to the invention can include further active ingredients and additives. It is therefore preferred within the scope of the present invention if the cosmetic agent additionally includes at least one further compound selected from the group of (i) thickening agents; (ii) linear or branched, saturated or unsaturated alcohols having 8 to 20 carbon atoms; (iii) surfactants, in particular amphoteric surfactants; (iv) alkalizing agents; (v) oils; and (vi) mixtures thereof.

The cosmetic agents according to the invention are preferably formulated as flowable preparations. Here, the cosmetic agents should be formulated such that they can be easily applied at the site of application, but are also sufficiently viscous so that they remain at the site of action during the treatment time and do not run.

It has therefore proven to be advantageous in accordance with the invention if the cosmetic agents according to the invention include at least one thickening agent from the group of (i) anionic, synthetic polymers; (ii) cationic, synthetic polymers; (iii) naturally occurring thickening agents, such as non-ionic guar gum, scleroglucan gum, or xanthan gum, gum arabic, ghatti gum, karaya gum, tragacanth gum, carrageenan gum, agar agar, locust bean gum, pectins, alginates, starch fractions, and derivatives such as amylose, amylopectin and dextrins and also cellulose derivatives, such as methyl cellulose, carboxy alkyl celluloses and hydroxy alkyl cellulose; (iv) non-ionic synthetic polymers, such as polyvinyl alcohol or polyvinyl pyrrolidone; (v) inorganic thickening agents, in particular sheet silicates, such as bentonite, in particular smectites, such as montmorillonite or hectorite; and (vi) mixtures thereof, in a total amount of from 0.0005 to 5.0% by weight, preferably from 0.001 to 3.0% by weight, preferably from 0.005 to 1.0% by weight, in particular from 0.008 to 0.01% by weight, in relation to the total weight of the cosmetic agent.

It has proven to be particularly advantageous within the scope of the present invention if at least one naturally occurring thickening agent, in particular xanthan gum and salts thereof, is included as thickening agent, in a total amount of from 0.005 to 0.5% by weight, in particular from 0.01 to 0.1% by weight, in relation to the total weight of the cosmetic agent.

Within the scope of the present invention it can be preferred if the linear or branched, saturated or unsaturated alcohol having 8 to 20 carbon atoms is selected from the group of myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), preferably 2-octyldodecanol and/or cetearyl alcohol and is included in a total amount by weight of from 1.0 to 35% by weight, preferably from 5.0 to 30% by weight, preferably from 10 to 25% by weight, in particular from 12 to 20% by weight, in relation to the total weight of the cosmetic agent.

The cosmetic agents according to the invention can preferably also include at least one partial ester from a polyol having 2 to 6 carbon atoms and linear saturated carboxylic acids having 12 to 30 atoms, in particular 14 to 22 carbon atoms, wherein the partial ester(s) can be hydroxylated, in a total amount of from 0.5 to 10% by weight, in particular from 3.0 to 8.0% by weight, in relation to the total weight of the cosmetic agent. Such partial esters are in particular the mono- and diesters of glycerol or the monoesters of propylene glycol or the mono- and diesters of ethylene glycol or the mono-, di-, tri- and tetraesters of pentaerythrite, in each case with linear saturated C12-C30 carboxylic acids, which can be hydroxylated, in particular those with palmitic and stearic acid, the sorbitan mono-, di-, or triesters of linear saturated C12-C30 carboxylic acids, which can be hydroxylated, in particular those of myristic acid, palmitic acid, stearic acid, or of mixtures of these fatty acids and the methylglucose mono- and diesters of linear saturated C12-C30 carboxylic acids, which can be hydroxylated.

Within the scope of the present invention, it can be provided that the cosmetic agents according to the invention include at least one polyol partial ester, selected from glycerol monostearate, glycerol monopalmitate, glycerol dipalmitate, ethylene glycol monostearate, ethylene glycol monopalmitate, ethylene glycol distearate, ethylene glycol dipalmitate, and mixtures hereof, in particular mixtures of glycerol monostearate, glycerol monopalmitate, glycerol distearate, and glycerol dipalmitate in a total amount of from 0.5 to 10% by weight, in particular from 3.0 to 8.0% by weight, in relation to the total weight of the cosmetic agent.

The use of the aforementioned alcohols, partial esters and polypartial esters in the cosmetic agents according to the invention can be preferred in particular when the cosmetic agents according to the invention are present in the form of an oil-in-water emulsion.

It can also be provided in accordance with the invention that the cosmetic agents include at least one surfactant in accordance with the invention. Surfactants within the sense of the present invention are amphiphilic (bifunctional) compounds which consist of at least one hydrophobic and at least one hydrophilic molecule part. A basic property of surfactants and emulsifiers is the oriented absorption at interfaces and also the aggregation into micelles and the formation of lyotropic phases.

In accordance with a preferred embodiment of the present invention, the cosmetic agents according to the invention include at least one amphoteric surfactant in a total amount of from 0.1 to 5.0% by weight, in particular from 0.2 to 2.0% by weight, in relation to the total weight of the cosmetic agent. Amphoteric or zwitterionic surfactants refer to surface-active compounds which have at least one quaternary ammonium group and at least one —COO(—) group or —SO3(—) group.

Within the scope of the present invention, the following compounds are particularly preferred as amphoteric surfactants:
  alkyl betaines having 8 to 20 carbon atoms in the alkyl group,
  amidopropyl betaines having 8 to 20 carbon atoms in the acyl group, sulfobetaines having 8 to 20 carbon atoms in the acyl group, and amphoacetates or amphodiacetates having 8 to 20 carbon atoms in the acyl group.

In a particularly preferred embodiment the cosmetic agents according to the invention include, as surfactant, at least one amphoteric surfactant, selected from amidopropyl betaines having 9 to 13 carbon atoms in the acyl group, in a total amount of from 0.1 to 5.0% by weight, in particular from 0.2 to 2.0% by weight, in relation to the total weight of the cosmetic agent.

It can also be provided that the cosmetic agents according to the invention include at least one ethoxylated non-ionic surfactant in a total amount of from 0.5 to 6.0% by weight, in particular from 1.0 to 4.0% by weight, in relation to the total weight of the cosmetic agent. Here, it has proven to be particularly advantageous if the ethoxylated non-ionic surfactant has an HLB value of more than 10, preferably more than 13. To this end, it is necessary that the non-ionic surfactant has a sufficiently high degree of ethoxylation. In this regard, the cosmetic agent according to the invention therefore includes, as ethoxylated non-ionic surfactant, at least one ethoxylated surfactant having at least 12 ethylene oxide units. Besides the accordingly ethoxylated fatty alcohols, in particular lauryl alcohol, myristyl alcohol, cetyl alcohol, stearyl alcohol, arachyl alcohol and behenyl alcohol, the addition products of from 20 to 60 mol ethylene oxide with castor oil and hardened castor oil in particular are particularly suitable in accordance with the invention. The at least one ethoxylated non-ionic surfactant is preferably selected from surfactants having the INCI name Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil and PEG-60 Hydrogenated Castor Oil, and mixtures of these substances, particularly preferably selected from Ceteth-20, Steareth-20, Ceteareth-20, Ceteth-30, Steareth-30 and Ceteareth-30.

Cosmetic agents within the scope of the present invention generally have an alkaline pH value, in particular between pH 8.0 and pH 12. These pH values are necessary in order to ensure an opening of the outer cuticle layer (cuticula) and to permit a penetration of the oxidation dye precursors and/or of the oxidizing agent into the hair.

The aforementioned pH value can preferably be set with use of an alkalizing agent. Within the scope of the present invention, the alkalizing agent is selected from the group of (i) inorganic alkalizing agents; (ii) organic alkalizing agents; and (iii) mixtures thereof, and is included in a total amount of from 1.5 to 9.5% by weight, preferably from 2.5 to 8.5% by weight, preferably from 3.0 to 8.0% by weight, in particular from 3.5 to 7.5% by weight, in relation to the total weight of the cosmetic agent.

Preferred inorganic alkalizing agents are selected from the group which is formed from ammonia or ammonium hydroxide, i.e. aqueous solutions of ammonia, sodium hydroxide, potassium hydroxide, calcium hydroxide, barium hydroxide, sodium phosphate, potassium phosphate, sodium silicate, potassium silicate, sodium carbonate and potassium carbonate as well as mixtures hereof. Ammonia or ammonium hydroxide is a particularly preferred alkalizing agent. Ammonia is particularly preferably included in a total amount of from 0.1 to 20% by weight, preferably from 0.5 to 10% by weight, in particular from 1.0 to 7.0% by weight, in relation to the total weight of the cosmetic agent.

Preferred organic alkalizing agents are selected from at least one alkanolamine. Alkanolamines that are preferred in accordance with the invention are selected from alkanolamines from primary, secondary or tertiary amines having a C2-C6 alkyl main structure carrying at least one hydroxyl group. Particularly preferred alkanolamines are selected from the group formed from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropan-1,2-diol, 2-amino-2-methylpropan-1,3-diol, 2-amino-2-ethyl-1,3-propanediol, N,N-dimethylethanolamine, triethanolamine, diethanolamine and triisopropanolamine. Alkanolamines that are very particularly preferred in accordance with the invention are selected from the group of 2-aminoethan-1-ol (monoethanolamine), 2-amino-2-methylpropan-1-ol, 2-amino-2-methylpropan-1,3-diol and triethanolamine. Particularly preferred cosmetic agents according to the invention include a mixture of monoethanolamine and 2-amino-2-methylpropan-1-ol. The at least one alkanolamine is preferably included in a total amount of from 0.05 to 15% by weight, preferably from 0.5 to 10% by weight, in particular from 3.5 to 7.5% by weight, in relation to the total weight of the cosmetic agent.

Further organic alkalizing agents that are preferred in accordance with the invention are selected from basic amino acids, particularly preferably selected from the group formed from L-arginine, D-arginine, D/L-arginine, L-lysine, D-lysine, D/L-lysine, and mixtures thereof. Basic amino acids that are particularly preferred in accordance with the invention are selected from L-arginine, D-arginine and D/L-arginine. Preferred cosmetic agents according to the invention include at least one alkalizing agent different from alkanolamines and ammonia in a total amount of from 0.05 to 5.0% by weight, in particular from 0.5 to 3.0% by weight, in relation to the total weight of the cosmetic agent.

In accordance with the invention, the alkalizing agent is preferably selected from the group of sodium hydroxide, potassium hydroxide, ammonia, monoethanolamine and 2-amino-2-methylpropane, preferably monoethanolamine, and is included in a total amount of from 1.5 to 9.5% by weight, preferably from 2.5 to 8.5% by weight, preferably from 3.0 to 8.0% by weight, in particular from 3.5 to 7.5% by weight, in relation to the total weight of the cosmetic agent.

In a particularly preferred embodiment, the cosmetic agents according to the invention include, as alkalizing agent, a mixture of at least two alkanolamines different from each other, in particular a mixture of monoethanolamine and 2-amino-2-methylpropan-1-ol, in a total amount of from 0.05 to 15% by weight, preferably from 0.5 to 10% by weight, in particular from 3.5 to 7.5% by weight, in relation to the total weight of the cosmetic agent.

The pH value of the cosmetic agents according to the invention, measured at 22° C., is preferably 8 to 13, preferably 9.5 to 12, preferably 10 to 11.5, in particular 10.5 to 11.

Within the scope of the present invention it can also be preferable if the cosmetic agents according to the invention include at least one oil, selected from the group of sunflower oil, corn oil, soybean oil, pumpkin seed oil, grape seed oil, sesame oil, hazelnut oil, apricot kernel oil, macadamia nut oil, arara oil, castor oil, avocado oil and mixtures thereof in a total amount of from 0.1 to 10% by weight, preferably from 0.2 to 5.0% by weight, in particular from 0.5 to 2.0% by weight, in relation to the total weight of the cosmetic agent. The care effect of the aminated silicone polymers can be further increased by the use of at least one of the aforementioned oils.

The cosmetic agents according to the invention particularly preferably include grape seed oil in a total amount of from 0.1 to 10% by weight, preferably from 0.2 to 5.0% by weight, in particular from 0.5 to 2.0% by weight, in relation to the total weight of the cosmetic agent.

In accordance with a particularly preferred embodiment of the present invention, the cosmetic agents according to the invention present in the form of an oil-in-water emulsion include—in relation to the total weight of the cosmetic agents octyldodecanol in a total amount of from 2.0 to 20% by weight, in particular from 5.0 to 12% by weight, and also mixtures of glycerol monostearate, glycerol monopalmitate, glycerol distearate and glycerol dipalmitate in a total amount of from 0.5 to 10% by weight, preferably 3.0 to 8.0% by weight, and also at least one amphoteric surfactant, selected from amidopropyl betaines having 9 to 13 carbon atoms in the acyl group, in a total amount of from 0.1 to 5.0% by weight, in particular from 0.2 to 2.0% by weight, and also a mixture of at least two different amidopropyl betaines, in particular of monoethanolamine and 2-amino-2-methylpropan-1-ol, in a total amount of from 0.05 to 15% by weight, preferably from 0.5 to 10% by weight, in particular from 3.5 to 7.5% by weight, and also grape seed oil in a total amount of from 0.1 to 10% by weight, preferably from 0.2 to 5.0% by weight, in particular from 0.5 to 2.0% by weight.

Oxidative lighteners can also be produced directly prior to the application from two or more separately packaged compositions. This lends itself in particular for the separation of incompatible ingredients, so as to avoid a premature reaction. A separation into multi-component systems is preferred in particular where incompatibilities of the ingredients are anticipated or feared. The oxidative lightener is in these cases produced by the consumer immediately prior to the application by mixing the components. Within the scope of the present invention, this approach is particularly preferred in the case of oxidative lighteners where the cosmetic agent according to the invention is initially provided separate from an oxidizing agent preparation including at least one oxidizing agent.

A further subject of the present invention is therefore a packaging unit (kit of parts), comprising—packaged separately from one another a) at least one container (C1), including a cosmetic agent according to the invention, and b) at least one container (C2), including an oxidizing agent preparation which includes at least one oxidizing agent in a cosmetically acceptable carrier.

The term "container" is understood within the scope of the present invention to mean a wrapping which is provided in the form of a bottle, a tube, a can, a pouch, a sachet, or the like, which is re-closable as appropriate. The wrapping material is not subject to any limitations in accordance with the invention. However, wrappings made of glass or plastic are preferably used.

Within the scope of the present invention, the oxidizing agents are different from atmospheric oxygen. Hydrogen peroxide and also the solid addition products thereof with organic and inorganic compounds can be used as oxidizing agents. In particular, the addition products of urea, melamine, polyvinylpyrrolidone and also sodium borate are potential solid addition products in accordance with the invention. Hydrogen peroxide and/or one of the fixed addition products thereof with organic or inorganic compounds are particularly preferred as oxidizing agents. In accordance with the invention, the oxidizing agent is therefore preferably selected from the group of persulfates, chlorites, hydrogen peroxide and addition products of hydrogen peroxide with urea, melamine and sodium borate, in particular hydrogen peroxide.

A particularly preferred embodiment of the present invention is thus characterized in that hydrogen peroxide is included as oxidizing agent, in a total amount of from 0.5 to 20% by weight, preferably from 2.0 to 15% by weight, preferably from 3.0 to 12% by weight, particularly preferably from 4.0 to 10% by weight, in particular from 5.5 to 9.0% by weight, in relation to the total weight of the oxidizing agent preparation. Here, the calculation of the total amount is based on 100% $H_2O_2$.

The oxidizing agent preparations can also include water in a total amount of from 40 to 98% by weight, in particular from 65 to 85% by weight, in relation to the total weight of the oxidizing agent preparation.

In accordance with a preferred embodiment of the present invention, the oxidizing agent preparations also include at least one linear saturated alkanol having 12 to 30 carbon atoms, in particular having 16 to 22 carbon atoms, in a total amount of from 0.1 to 10% by weight, preferably from 0.5 to 5.0% by weight, in particular from 1.0 to 4.0% by weight, in relation to the total weight of the oxidizing agent preparation. In particular, cetyl alcohol, stearyl alcohol, arachidyl alcohol, behenyl alcohol and lanolin alcohol or mixtures of these alcohols, as are obtainable in the case of industrial hydrogenation of vegetable and animal fatty acids, are preferred, as well as mixtures of these alkanols. The mixture cetearyl alcohol is particularly preferred.

In a further preferred embodiment of the present invention, the oxidizing agent preparations include at least one ethoxylated non-ionic surfactant, which is preferably selected from surfactants having the INCI name Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil and PEG-60 Hydrogenated Castor Oil, and mixtures of these substances, particularly preferably selected from Ceteth-20, Steareth-20, Ceteareth-20, Ceteth-30, Steareth-30 and Ceteareth-30, in a total amount of from 0.1 to 10% by weight, preferably from 0.5 to 5.0% by weight, in particular from 1 to 4.0% by weight, in relation to the total weight of the oxidizing agent preparation.

Within the scope of the present invention, it can additionally be provided that the oxidizing agent preparations include at least one ester from a carboxylic acid having 10 to 20 carbon atoms and a linear or branched alcohol having 1 to 5 carbon atoms, in particular isopropylmyristate, in a total amount of from 3.0 to 25% by weight, preferably from 5.0 to 20% by weight, in particular from 8.0 to 15% by weight, in relation to the total weight of the oxidizing agent preparation.

In accordance with a particularly preferred embodiment of the present invention, the oxidizing agent preparations include—in relation to the total weight of the oxidizing agent preparations— at least one linear saturated alkanol having 12 to 30 carbon atoms in a total amount of from 0.1 to 10% by weight, preferably from 0.5 to 5.0% by weight, in particular from 1.0 to 4.0% by weight, and also at least one ethoxylated non-ionic surfactant, which is preferably selected from surfactants having the INCI name Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil and PEG-60 Hydrogenated Castor Oil, and mixtures of these substances, particularly preferably selected from Ceteth-20, Steareth-20, Ceteareth-20, Ceteth-30, Steareth-30 and Ceteareth-30, in a total amount of from 0.1 to 10% by weight, preferably from 0.5 to 5.0% by weight, in particular from 1 to 4.0% by weight, and also at least one ester from a carboxylic acid having 10 to 20 carbon atoms and a linear or branched alcohol having 1 to 5 carbon atoms, preferably isopropylmyristate, in a total amount of from 3.0 to 25% by weight, preferably from 5.0 to 20% by weight, in particular from 8.0 to 15% by weight.

The oxidizing agent preparations according to the invention also include at least one acid. Preferred acids are selected from dipicolinic acid, edible acids, such as citric acid, acetic acid, malic acid, lactic acid and tartaric acid, diluted mineral acids, such as hydrochloric acid, phosphoric acid, pyrophosphoric acid and sulfuric acid, and mixtures hereof. The oxidizing agent preparations preferably have a pH value ranging from 2 to 5, in particular from 3 to 4.

In order to produce oxidative lighteners from the packaging unit (kit of parts) according to the invention, the cosmetic agent according to the invention is mixed in the container C1 with the oxidizing agent preparation in the container C2 or vice versa.

It can also be particularly advantageous in accordance with the invention if the packaging unit includes at least one further hair treatment agent, in particular a conditioning agent preparation, in an additional container. This conditioning agent preparation advantageously includes at least one conditioning agent, selected from the group of cationic polymers, silicone derivatives, and oils. In addition, the packaging unit can comprise application aids, such as combs, brushes, tint applicators or paintbrushes, personal protective equipment, in particular disposable gloves, and, as appropriate, a set of instructions. A tint applicator is understood to mean a broad paintbrush, at the stem end of which there is a tip which permits and facilitates the sectioning of fiber bundles or strands from the total amount of fibers.

With regard to the cosmetic agent according to the invention in the container C1 and the oxidizing agent preparation in the container C2, that which has been said in relation to the cosmetic agents according to the invention applies mutatis mutandis.

A further subject of the present invention is a method for dyeing, in particular for lightening keratin fibers, wherein the method comprises the following method steps:

a) providing a cosmetic agent (M1) according to the invention,
b) providing an oxidizing agent preparation (M2), including at least one oxidizing agent in a cosmetically acceptable carrier,
c) mixing the cosmetic agent (M1) with the oxidizing agent preparation (M2),
d) applying the mixture obtained in step c) to the keratin fibers and leaving this mixture on the keratin fibers for between 10 and 60 minutes, preferably between 20 and 45 minutes, at room temperature and/or at least at 45° C.,
e) rinsing the keratin fibers with water and/or a cleaning composition for 1 to 5 minutes, and
f) optionally applying a post-treatment agent to the keratin fibers and rinsing this out after a period of from 1 to 10 minutes.

The method according to the invention for dyeing, in particular for lightening keratin fibers with use of a specific aminated silicone polymer results in an improved care of dyed keratin fibers with improved lightening performance.

Here, within the scope of the present invention, room temperature is understood to mean the ambient temperature that prevails without influence of external heat and is preferably from 10 to 39° C. The effect of the lightening preparation can be intensified by application of external heat, for example by means of a heat hood. The preferred period of action of the lightening preparation on the keratin fibers is 10 to 60 minutes, preferably 20 to 45 minutes. Once the period of action is complete, the remaining lightening agent is washed out from the keratin fibers with the aid of a cleaning preparation preferably including at least one cationic and/or anionic and/or non-ionic surfactant, and/or water. The process is optionally repeated with a further agent. Once the agent has been washed out, the keratin fibers are optionally rinsed with a post-treatment agent, for example a conditioning means, and dried using a towel or a hot air blower. The lightening composition is usually applied by hand by the user. Personal protective equipment is preferably worn, in particular suitable protective gloves, for example made of plastic or Latex, for one-time use (disposable gloves), and an apron if necessary. However, it is also possible to apply the dyes to the keratin fibers using an application aid.

Particularly preferred methods according to the invention are characterized in that the methods result in improved care of the keratin fibers with improved lightening performance. Due to the use of at least one specific aminated silicone polymer, the care and lightening performance resulting from the method according to the invention is greater than the care and lightening performance which can be achieved in the absence of the aminated silicone polymer b) used in accordance with the invention.

With regard to the cosmetic agent M1 according to the invention, the oxidizing agent preparation M2 and also further preferred embodiments of the method according to the invention, that said in relation to the cosmetic agents according to the invention and also the packaging unit according to the invention applies mutatis mutandis.

In addition, a further subject of the present invention is the use of a cosmetic agent according to the invention for increasing the care of keratin fibers with improved lightening performance. The use of a specific aminated silicone polymer results in an increased care of dyed keratin fibers with improved lightening performance.

With regard to further preferred embodiments of the use according to the invention, that said in relation to the cosmetic agents according to the invention and also the packaging unit according to the invention applies mutatis mutandis.

In addition, a further subject of the present invention is the use of a packaging unit according to the invention for producing a cosmetic agent for changing the color of, in particular for lightening keratin fibers with increased care of the keratin fibers with improved lightening performance. The use of a specific aminated silicone polymer results in an increased care of dyed keratin fibers with improved lightening performance.

With regard to further preferred embodiments of the use according to the invention, that said in relation to the cosmetic agents according to the invention and also the packaging unit according to the invention applies mutatis mutandis.

The following examples are intended to explain preferred embodiments of the invention, but without limiting the invention thereto.

EXAMPLES

1. Formulations

Compositions of the used cosmetic agents (oil-in-water emulsions, all amounts in % by weight). The aminated silicone polymer used in the following formulations is preferably a silicone polymer of formula (III) with n=2 or 3 and a mean molecular weight Mw of 1,000 to 200,000 Da.

| Raw material | V1 | E1* | E2* |
| --- | --- | --- | --- |
| Xanthan gum | 0.05 | 0.05 | 0.05 |
| 2-octyldodecanol | 2.3 | 2.3 | 2.3 |
| Lanette N[a)] | 14 | 14 | 14 |
| Cetearyl alcohol | 3.9 | 3.9 | 3.9 |
| Glycerol monostearate | 6.0 | 6.0 | 6.0 |
| Glycerol 99.5% | 2.0 | 2.0 | 2.0 |
| Cocoamidopropyl betaine, 40% | 2.0 | 2.0 | 2.0 |
| Monoethanolamine | 6.1 | 6.1 | 6.1 |
| 2-amino-2-methylpropanol | 0.1 | 0.1 | 0.1 |
| Sodium sulfite, anhydrous | 0.1 | 0.1 | 0.1 |
| Caramel syrup, 75% | 0.1 | 0.1 | 0.1 |
| Grape seed oil | 1.0 | 1.0 | 1.0 |
| p-toluenediamine sulfate | 0.09 | 0.09 | 0.09 |
| 1,3-benzenediol | 0.02 | 0.02 | 0.02 |
| 3-aminophenol | 0.003 | 0.003 | 0.003 |
| 4-chlororesorcinol | 0.03 | 0.03 | 0.03 |
| Aminated silicone polymer** | — | 0.97 | 1.9 |
| Water, demineralized | to 100.00 | to 100.00 | to 100.00 |

*according to the invention
**active substance
[a)]INCI name: Cetearyl alcohol, Sodium cetearyl sulfate (BASF)

The fat base was in each case fused together at 80° C. and dispersed with a proportion of the water quantity. The rest of the formulation constituents were then incorporated in order, with stirring. The mixture was then made up to 100% by weight with water, and the formulation was stirred cold. Formulation V1 was a comparative formulation not according to the invention, without aminated silicone polymer. Formulations E1 and E2 are examples according to the invention. Oxidizing agent preparation O1 (all amounts in % by weight)

| Raw material | O1 |
| --- | --- |
| Disodium pyrophosphate | 0.10 |
| Dipicolinic acid | 0.10 |
| Potassium hydroxide 50% | 0.23 |
| 1-hydroxyethan-1,1-diphosphonic acid 60% | 0.25 |
| Emulgade F[b)] | 4.0 |
| Cetearyl alcohol | 0.5 |
| Ceteareth-20 | 0.5 |
| Beeswax | 0.3 |
| Isopropylmyristate | 10 |
| Hydrogen peroxide 50% | 23 |
| Water, demineralized | to 100 |

[b)]INCI name: Cetearyl alcohol, PEG-4- Castor oil, Sodium cetearyl sulfate (BASF)

2. Improved Care by Addition of at Least One Specific Aminated Silicone Polymer

In order to produce the oxidative lightening agent for determining care, the cosmetic agents V1, E1 and E2 were each mixed in a ratio by weight of 1:2 with the above oxidizing agent preparation O1.

12 strands of naturally light-brown European hair (IHIP (New York), batch #03/2012, N121, length 15 cm, weight 1 g) were washed with an aqueous sodium lauryl ether sulfate solution (3% active substance content in the solution). The strands were dried in air and stored for 24 h at 25° C. and relative ambient humidity. Once these strands had been soaked in water for 5 minutes, the wet combability thereof was determined (reference value).

For the dyeing operations, 12 strands of natural European hair (IHIP (New York), batch #03/2012, N121, length 15 cm, weight 1 g) were used in each case per oxidative dye. For this purpose, 4 g of the previously produced oxidative lightening agents were applied in each case per 1 g of hair strands. Once the strands had been dyed for 30 minutes at 32° C., they were rinsed for 2 minutes with water and dried in air.

The wet combability was measured as follows:

Before the measurement, each strand was wetted for 2 seconds with water by combing with a hard rubber comb with fine teeth (Hercules Sägemann, Hamburg Germany). After 3 combing operations, the combing force was measured during a further 10 combing operations, wherein the hair strands were rotated slowly during the combing operation. The measured values obtained were compared with use of the following statistical tests embedded in the software Statistica 10.0 (StatSoft Inc., USA):

Shapiro-Wilks test (test for normal distribution)
Grubbs' test for outliers
Bartlett test (test of homoscedasticity)
Univariate significance test
Newman-Keuls test (determination of significant differences)
Unequal N HSD test (test of multiple comparisons).

The change in combing force dK in % can be calculated with the aid of the formula dK=[K0−Ki]/K0]*100. Here, K0 is the mean value of the combing force for the un-dyed hair strands, and Ki is the mean value for the hair strands treated with the particular oxidative lighteners.

The care of the hair strands is greater, the lower is the applied combing force, and therefore the higher is the change in the combing force. The dK values for the colorings with use of the cosmetic agents V1, E1 and E2 are presented in Table 2. The colorings with the cosmetic agents E1 and E2 according to the invention, which include at least one specific aminated silicone polymer in a total amount of from 0.7% by weight and 1.9% by weight respectively, have a higher change to the combing force and therefore increased care compared to the colorings without aminated silicone polymer (V1).

| Oxidative dye | dK [%] |
| --- | --- |
| V1 + O1 (1:2) | 23 |
| E1 + O1 (1:2) | 42 |
| E2 + O1 (1:2) | 40 |

3. Improved Lightening by Addition of at Least One Specific Aminated Silicone Polymer For the lightening process, 4 times the amount of the oxidative lightener produced under point 2. was applied to strands of dark-blond, light-brown and dark-brown hair (Codes: Kerling 6/0, Fischbach & Miller 6923). Once the strands had been bleached for 45 minutes at 32° C., they were washed using a commercially available shampoo and dried using a hairdryer.

All strands were measured using a color measuring apparatus from Datacolor of the Spectraflash 450 type. The value dL used for the assessment of lightening performance was given as follows from the L*a*b measured color values measured on the respective strands:

$$dL = Li - L0$$

L0 here is the mean value of the measured color values of the untreated hair strands determined from the 12 measurements, whereas Li is the mean value of the measured color values after the lightening of the hair strands with the respective oxidative lighteners.

The higher is the dL value, the higher is the lightening performance of the corresponding cosmetic agent. The following table presents the dL values for the colorings with use of the cosmetic agents V1, E1 and E2. The colorings with the cosmetic agents E1 and E2 according to the invention, which include at least one aminated silicone polymer in a total amount of from 0.97% by weight and 1.9% by weight respectively, had an improved lightening performance compared to the coloring without aminated silicone polymer (V1).

| Oxidative lightener | dL |
| --- | --- |
| V1 + O1 (1:2) | 5.87 |
| E1 + O1 (1:2) | 7.27 |
| E2 + O1 (1:2) | 6.27 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A cosmetic agent for changing the color of keratin fibers, comprising, in a cosmetically acceptable carrier:
   a) at least one compound, selected from the group consisting of: oxidative dye precursors, direct dyes, and mixtures thereof,
   b) at least one aminated silicone polymer, including at least one structural unit of the formula (I) and at least one structural unit of formula (II)

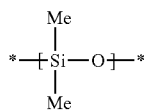

(I)

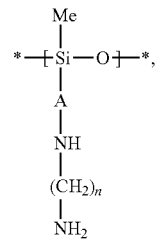

(II)

in which
A stands for a linear or branched $C_4$-$C_8$ alkyl group, and
n stands for integers from 1 to 4, and
a cyclic aminated silicone polymer in a total amount of from 0.003 to 1.5% by weight in relation to the total weight of the cosmetic agent, wherein the cyclic aminated silicone polymer has the formula (IV)

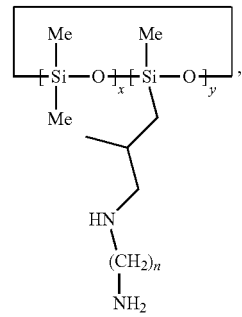

(IV)

in which
x stands for integers from 0 to 1,999;
wherein the cosmetic agent does not include any acid selected from the group consisting of: carboxylic acids having 8 to 30 carbon atoms, the ether carboxylic acids having 8 to 30 carbon atoms, the ether phosphoric acids having 8 to 30 carbon atoms, the phosphoric acids having 8 to 30 carbon atoms, and mixtures thereof.

2. The cosmetic agent according to claim 1, wherein the structural unit of formula (II), n stands for the integer 2 or 3, and A stands for a branched C4 alkyl group.

3. The cosmetic agent according to claim 1, wherein the cosmetic agent includes at least one aminated silicone polymer of formula (III)

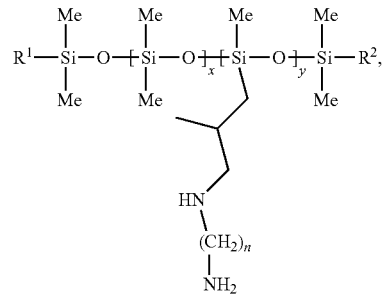

(III)

in which
$R^1$ and $R^2$, each independently of one another, stand for a methyl group or a hydroxyl group, x stands for integers from 0 to 1,999, y stands for integers from 1 to 200, and n stands for integers from 1 to 5.

4. The cosmetic agent according to claim 1, wherein the at least one aminated silicone polymer b) has a mean molecular weight $M_w$ of from 350 to 350,000 Da.

5. The cosmetic agent according to claim 1, wherein the at least one aminated silicone polymer b) has a mean molecular weight $M_w$ of 1,000 to 200,000 Da.

6. The cosmetic agent according to claim 1, wherein the at least one aminated silicone polymer b) has an amine value of from 0.25 to 5 meq/g.

7. The cosmetic agent according to claim 1, wherein the at least one aminated silicone polymer b) has an amine value of from 0.5 to 1.5 meq/g.

8. The cosmetic agent according to claim 1, wherein the cosmetic agent includes the at least one aminated silicone polymer b) in a total amount of from 0.0001 to 15% by weight in relation to the total weight of the cosmetic agent.

9. The cosmetic agent according to claim 1, wherein the cosmetic agent includes the at least one aminated silicone polymer b) in a total amount of 0.05 to 1.0% by weight, in relation to the total weight of the cosmetic agent.

10. The cosmetic agent according to claim 1, wherein the cosmetic agent additionally includes dimethylcyclosiloxane in a total amount of less than 1% by weight, in relation to the total weight of the cosmetic agent, wherein the dimethylcyclosiloxane has the formula (V)

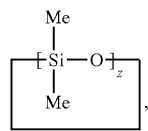

(V)

in which z stands for integers from 2 to 8.

11. The cosmetic agent according to claim 1, wherein the cosmetic agent additionally includes at least one further compound, selected from the group consisting of (i) thickening agents; (ii) linear or branched, saturated or unsaturated alcohols having 8 to 20 carbon atoms; (iii) surfactants; (iv) alkalizing agents; (v) oils; and (vi) mixtures thereof.

12. The cosmetic agent according to claim 11, wherein the cosmetic agent includes an alkalizing agent, said alkalizing agent being a mixture of at least two alkanolamines different from each other and comprising in total amount of 0.05 to 15% by weight of the cosmetic agent.

13. The cosmetic agent according to claim 11, wherein the alkalizing agent is a mixture of monoethanolamine and 2-amino-2-methylpropan-1-ol and comprises 0.5 to 10% by weight in relation to the total weight of the cosmetic agent.

14. A packaging unit (kit of parts), comprising—packaged separately from one another—
- a) at least one container (C1), including a cosmetic agent according to claim 1, and
- b) at least one container (C2), including an oxidizing agent preparation which includes at least one oxidizing agent in a cosmetically acceptable carrier.

15. The packaging unit (kit of parts) according to claim 14, wherein the oxidizing agent is hydrogen peroxide and is included in a total amount of from 0.5 to 20% by weight in relation to the total weight of the oxidizing agent preparation.

16. A method for dyeing keratin fibers, comprising:
- a) providing a cosmetic agent (M1) according to claim 1,
- b) providing an oxidizing agent preparation (M2), including at least one oxidizing agent in a cosmetically acceptable carrier,
- c) mixing the cosmetic agent (M1) with the oxidizing agent preparation (M2),
- d) applying the mixture obtained in step c) to the keratin fibers and leaving this mixture on the keratin fibers for between 10 and 60 minutes, at room temperature and/or at least at 45° C.,
- e) rinsing the keratin fibers with water and/or a cleaning composition for 1 to 5 minutes, and
- f) optionally applying a post-treatment agent to the keratin fibers and rinsing this out after a period of from 1 to 10 minutes.

* * * * *